United States Patent
Sobek et al.

(10) Patent No.: US 8,530,178 B2
(45) Date of Patent: Sep. 10, 2013

(54) HYDROLASE DETECTION SYSTEM WITH CAGED SUBSTRATES

(75) Inventors: Daniel Sobek, Portola Valley, CA (US); Jianghong Rao, Sunnyvale, CA (US)

(73) Assignee: Zymera, Inc., Portola Valley, CA (US)

( * ) Notice: Subject to any disclaimer, the term of this patent is extended or adjusted under 35 U.S.C. 154(b) by 360 days.

(21) Appl. No.: 12/445,378

(22) PCT Filed: Oct. 17, 2007

(86) PCT No.: PCT/US2007/081697
§ 371 (c)(1),
(2), (4) Date: Apr. 13, 2009

(87) PCT Pub. No.: WO2008/049036
PCT Pub. Date: Apr. 24, 2008

(65) Prior Publication Data
US 2010/0035290 A1 Feb. 11, 2010

Related U.S. Application Data

(60) Provisional application No. 60/829,877, filed on Oct. 17, 2006.

(51) Int. Cl.
*C12Q 1/42* (2006.01)
(52) U.S. Cl.
USPC .......................................................... 435/21
(58) Field of Classification Search
USPC ....................................... 435/21, 8
See application file for complete search history.

(56) References Cited

U.S. PATENT DOCUMENTS

| 2006/0099646 | A1 | 5/2006 | Heding |
| 2006/0105915 | A1* | 5/2006 | Naleway et al. .............. 504/117 |
| 2011/0097753 | A1* | 4/2011 | Wang et al. ....................... 435/8 |

FOREIGN PATENT DOCUMENTS
WO       WO 01/46691 A1    6/2001

OTHER PUBLICATIONS

Huang X. et al. A Resonance Energy Transfer Between Chemiluminescent Donors and Luminescent Quantum Dots as Acceptor. Angewandte Chemie 45, 5140-3, Jul. 7, 2005 first published online, here Aug. 4, 2006.*
John V. Frangioni, Self-illuminating quantum dots light the way, Nature Biotechnology, Mar. 2006, vol. 24(3), pp. 326-328.
Chenjie Xu et al., A self-assembled quantum dot probe for detecting b-lactamase activity, Biochemical and Biophysical Research Communication, Jun. 2006, vol. 344(3), pp. 931-935.
Robert R. Swezey and David Epel, The in vivo rate of glucose-6-phosphate dehydrogenase activity in sea urchin eggs determined with a photolabile caged substrate, Developmental Biology, Jun. 1995, vol. 169(2), pp. 733-744.
Yan Zhang et al., HaloTag protein-mediated site-specific conjugation of bioluminescent proteins to quantum dots, Angewandte Chemie International Edition, Jun. 2006, vol. 45, pp. 4936-4940.
Hequan Yao et al., A Bioluminogenic Substrate for In Vivo Imaging of Beta-Lactamase Activity, Angewandte Chemie International Edition, Aug. 2007, vol. 46, pp. 7031-7034.

* cited by examiner

*Primary Examiner* — Ralph Gitomer
(74) *Attorney, Agent, or Firm* — Ishimaru & Associates LLP

(57) ABSTRACT

An enzyme detection method includes forming a caged substrate; releasing an uncaged substrate by cleaving a caging molecule from the caged substrate; and emitting a light emission from a Bioluminescence Resonance Energy Transfer luminescent nanocrystal conjugate reacting with the uncaged substrate.

20 Claims, 3 Drawing Sheets

HYDROLASE DETECTION SYSTEM WITH CAGED SUBSTRATES

CROSS-REFERENCE TO RELATED APPLICATION(S)

This application is a U.S. national stage application which claims the benefit of the PCT application serial number PCT/US2007/081697 filed Oct. 17, 2007 which claims the benefit of U.S. Provisional Patent Application Ser. No. 60/829,877 filed Oct. 17, 2006.

TECHNICAL FIELD

The present invention relates to a system of caged substrates suitable for use in biochemical assays and more specifically to an enzyme detection system with caged substrates.

BACKGROUND ART

Enzyme activity measurements are clinical biomarkers for organ or muscle function. The detection principles disclosed in this document can be applied to hydrolases: enzymes that catalyze hydrolysis that results in the cleavage of an enzyme-specific side-group from the rest of the substrate. Examples include alkaline phosphatase (ALP), cholinesterase, and, esterase. ALP measurements are discussed in detail to illustrate the general detection method which may be applied for any of the mentioned enzymes. ALP is an enzyme included in standard liver panel assays and is a marker of cholestatic hepatoxicity. A higher than normal level of ALP may indicate that the subject of the test has liver disease, or cancer of the liver or bones.

Existing ALP assays measure enzyme activity using a chromogenic substrate consisting of 4-nitrophenyl phosphate. The chromogenic substrate, placed in an alkaline environment, changes to a yellow color in the presence of ALP. The color change is quantified by measuring the absorption spectrum using a spectrophotometer. Enzyme activity in chromogenic assays depends upon the reagent buffer's ability to revitalize the enzyme, pH, and the preservation of the blood specimen. Additional disadvantages of chromogenic assays are the production of precipitates that may interfere with enzyme activity thereby reducing sensitivity.

The chromogenic assays may be further complicated by interference caused by quenching from hemoglobin in red blood cells. This level of interference may reduce the sensitivity of chromogenic assays and possibly mask the presence of some low level enzymes.

Thus, a need still remains for an enzyme detection system with caged substrates that may improve the efficiency of whole blood assays. In view of the aging world population, it is increasingly critical that answers be found to these problems. With extended life expectancy and the development of many new drugs to support it, an efficient and cost effective enzyme detection system is a primary concern. Additionally, the need to save costs, improve efficiencies and performance, and meet competitive pressures, adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

The present invention provides an enzyme detection method including forming a caged substrate; releasing an uncaged substrate by cleaving a caging molecule from the caged substrate; and emitting a light emission from a Bioluminescence Resonance Energy Transfer luminescent nanocrystal conjugate reacting with the uncaged substrate.

The present invention provides an enzyme detection system including a caged substrate; an uncaged substrate released by a caging molecule cleaved from the caged substrate; and a light emission from a Bioluminescence Resonance Energy Transfer luminescent nanocrystal conjugate from the uncaged substrate reaction.

Certain embodiments of the invention have other aspects in addition to or in place of those mentioned above. The aspects will become apparent to those skilled in the art from a reading of the following detailed description when taken with reference to the accompanying drawings.

BEST MODE FOR CARRYING OUT THE INVENTION

Figure 1A:
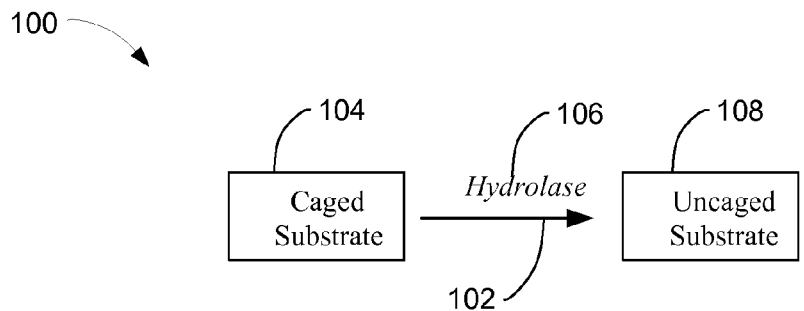
FIGS. 1A and 1B are a reaction diagram of a generalized assay for measuring hydrolase activity in whole blood, in an embodiment of the present invention.

The following embodiments are described in sufficient detail to enable those skilled in the art to make and use the invention. It is to be understood that other embodiments would be evident based on the present disclosure, and that process or mechanical changes may be made without departing from the scope of the present invention.

In the following description, numerous specific details are given to provide a thorough understanding of the invention. However, it will be apparent that the invention may be practiced without these specific details. In order to avoid obscuring the present invention, some well-known system configurations and process steps are not disclosed in detail. Likewise, the drawings showing embodiments of the system are semi-diagrammatic and not to scale and, particularly, some of the dimensions are for the clarity of presentation and are shown greatly exaggerated in the drawing FIGs. Where multiple embodiments are disclosed and described, having some features in common, for clarity and ease of illustration, description, and comprehension thereof, similar and like features one to another will ordinarily be described with like reference numerals.

For expository purposes, the term "horizontal" as used herein is defined as a plane parallel to the plane or contact surface of the platform, regardless of its orientation. The term "vertical" refers to a direction perpendicular to the horizontal as just defined. Terms, such as "above", "below", "bottom", "top", "side" (as in "sidewall"), "higher", "lower", "upper", "over", and "under", are defined with respect to the horizontal plane. The term "on" means there is direct contact among elements. The term "system" as used herein means and refers to the method and to the apparatus of the present invention in accordance with the context in which the term is used.

Figure 1B:
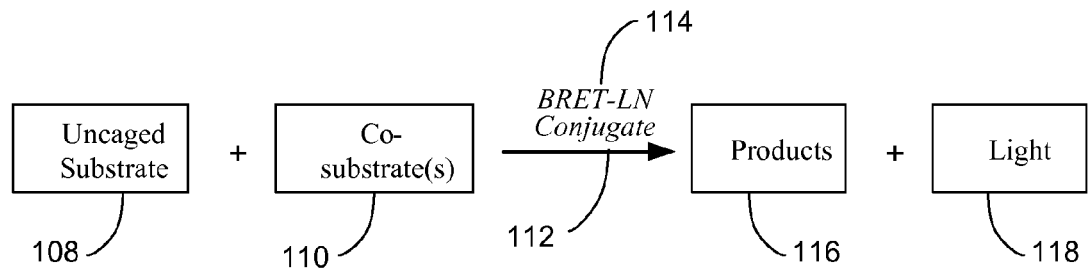

Referring now to FIGS. 1A and 1B, therein are shown a reaction diagram of a generalized assay for hydrolase 100 activity in whole blood, in an embodiment of the present invention. The reaction diagram of the generalized assay for hydrolase 100 depicts a first reaction 102 including a caged substrate 104. A caged substrate 104 is defined as the substrate for a bioluminescent molecule such as Renilla luciferase with a cleavable caging group that may be cleaved by the action catalyzed by a hydrolase enzyme 106. Hydrolases catalyze the hydrolysis of a chemical bond. The caged substrate 104 is not active as a substrate for a bioluminescent reaction. Once the caging group is removed by the hydrolase enzyme 106, the resulting uncaged substrate 108, is active as a substrate for the bioluminescent reaction.

Referring now to FIG. 1B, therein is shown the reaction diagram of the generalized assay for hydrolase 100. The reaction diagram of the generalized assay for hydrolase 100 depicts the uncaged substrate 108 combined with a co-substrate 110 and in a reaction 112 catalyzed by a Bioluminescence Resonance Energy Transfer luminescent nanocrystal (BRET-LN) conjugate 114. The BRET-LN conjugate 114 may include a luminescent nanocrystal (not shown) that may be made by linking Renilla luciferase (not shown) to a semiconductor nanostructure (not shown). The reaction 112 produces products 116 and a light emission 118 from the BRET-LN conjugate 114.

The BRET-LN conjugate 114 enables the light emission 118 in a wave length ranging from 600 nm to 900 nm. This range encompasses the red visible spectrum and the near infrared spectrum. The light emission 118 in this range of wavelengths may emit without significantly being quenched by hemoglobin in the blood or exciting autofluorescence from the blood proteins. This aspect of the invention allows highly sensitive assays without the requirement of separating the red cells from the blood.

Figure 2:
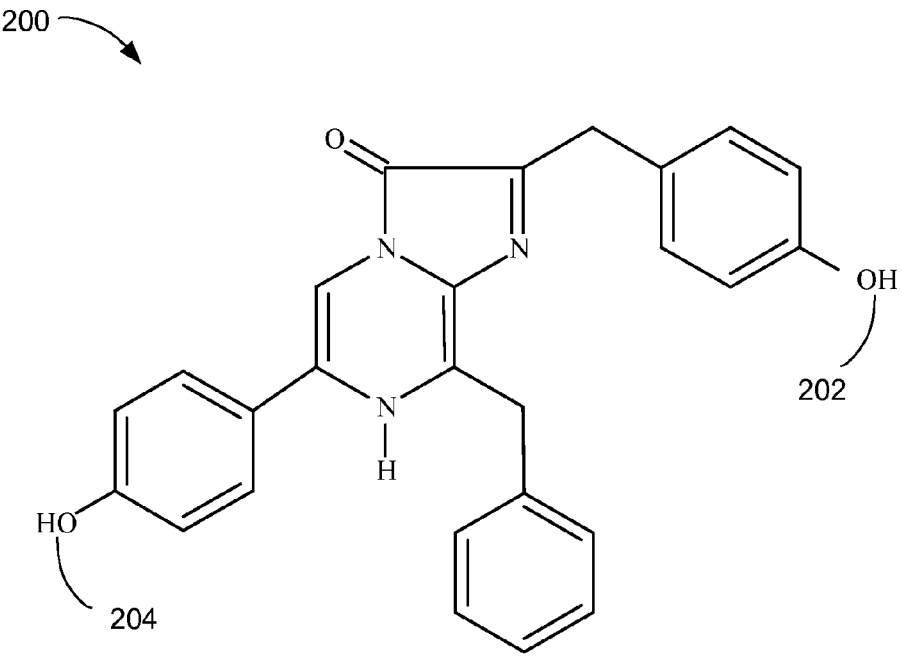
FIG. 2 is a bonding diagram of a coelenterazine molecule, having two positions where a caging group may be attached.

Referring now to FIG. 2, therein is shown a bonding diagram of a coelenterazine molecule 200, having two positions where a caging group may be attached. The bonding diagram of the coelenterazine molecule 200 depicts a first bonding site 202 and a second bonding site 204. The first bonding site 202 and the second bonding site 204 include hydroxyl groups. The coelenterazine molecule 200 may act as a substrate for activating Renilla luciferase (not shown) to produce the light emission 118, of FIG. 1.

Figure 3:
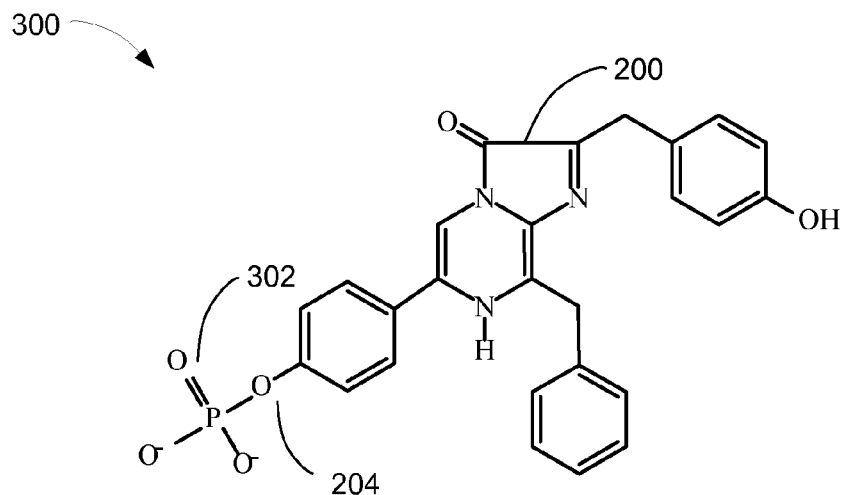
FIG. 3 is a bonding diagram of a caged coelenterazine molecule, having a phosphate group attached.

Referring now to FIG. 3, therein is shown a bonding diagram of a caged coelenterazine-phosphate molecule 300, having a phosphate group attached. The bonding diagram of the caged coelenterazine-phosphate molecule 300 depicts the coelenterazine molecule 200 having a caging molecule 302, such as a phosphate group, bonded to the second site 204. The caging molecule 302 replaces the hydroxyl group of the first bonding site 202 or the second bonding site of FIG. 2. The caged coelenterazine-phosphate molecule 300 is no longer capable of acting as a substrate for activating Renilla luciferase (not shown) to produce the light emission 118, of FIG. 1. As long as the caging molecule 302 is present the coelenterazine molecule 200 can not perform as a substrate to activate any luminescent enzyme. The caged coelenterazine-phosphate molecule 300 is also known as a caged substrate.

Figure 4A:
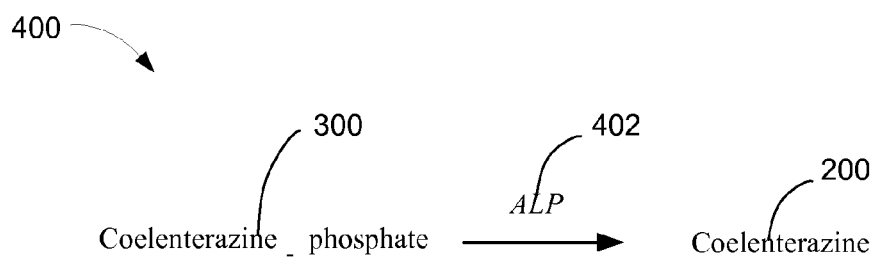
FIGS. 4A and 4B are a reaction diagram of an enzyme detection system with caged substrates, using the coelenterazine molecule, in an embodiment of the present invention.
Figure 4B:
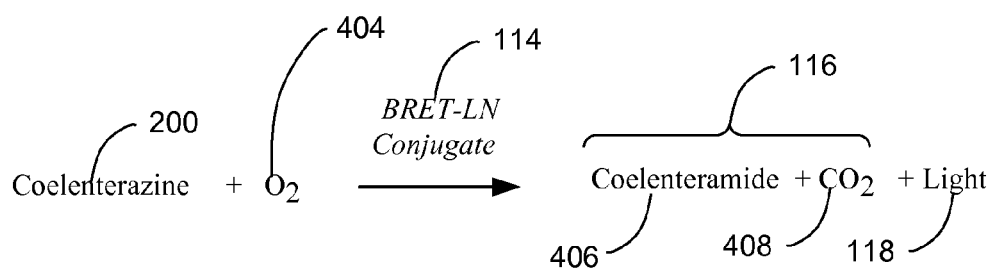

Referring now to FIGS. 4A and 4B, therein are shown a reaction diagram of an enzyme detection system 400 with caged substrates, using the coelenterazine molecule, in an embodiment of the present invention. The reaction diagram of FIG. 4A depicts the enzyme detection system 400 with caged substrates, including the caged coelenterazine-phosphate molecule 300. An alkaline phosphatase (ALP) molecule 402 catalyzes the cleavage of the caging molecule 302 and restores the coelenterazine molecule 200. In this reaction the limiting substance will be the alkaline phosphatase (ALP) molecule 402. Only a portion of the caged coelenterazine-phosphate molecules 300 will be cleaved by the alkaline phosphatase (ALP) molecules 402. The portion that is cleaved will be free to react in the next reaction as displayed in FIG. 4B. The remaining molecules of the caged coelenterazine-phosphate molecule 300 will remain inert in the reaction.

Referring now to FIG. 4B, therein is shown a reaction diagram of the enzyme detection system 400 with caged substrates. The reaction diagram of the enzyme detection system 400 depicts the coelenterazine molecule 200 that is in solution with an oxygen ($O_2$) molecule and catalyzed by the BRET-LN conjugate 114. The products 116 of the reaction include a coelenteramide molecule 406 and a carbon dioxide ($CO_2$) molecule 408. The light emission 118 will be correlated to the number of the coelenterazine molecule 200 that were liberated during the reaction of FIG. 4A. The amount of the light emission 118 will be indicative of the activity of the alkaline phosphatase (ALP) molecules 402 from the reaction of FIG. 4A.

Figure 5:
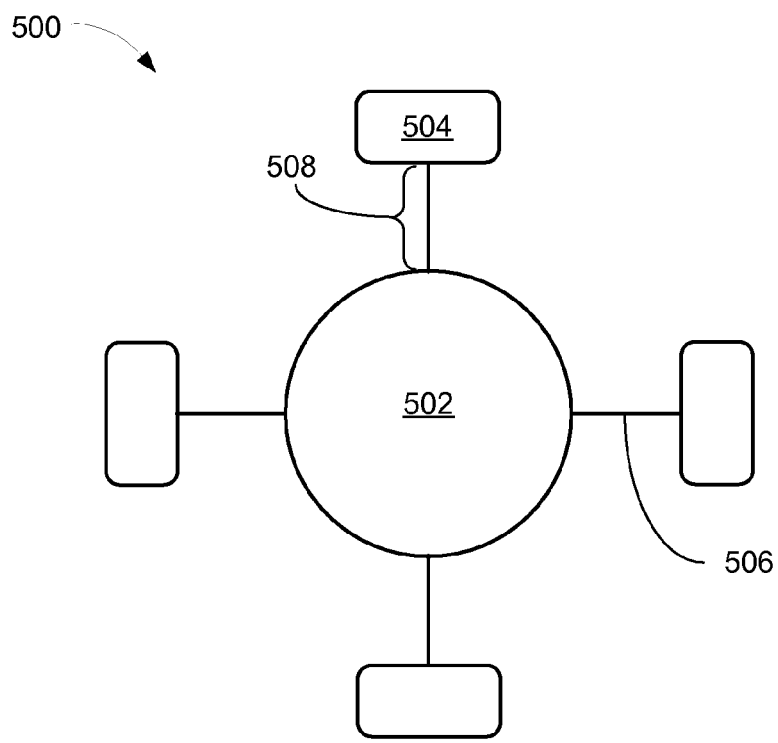
FIG. 5 is a block diagram of a Bioluminescence Resonance Energy Transfer luminescent nanocrystal (BRET-LN) conjugate, in an embodiment of the present invention.

Referring now to FIG. 5, therein is shown a block diagram of a Bioluminescence Resonance Energy Transfer luminescent nanocrystal (BRET-LN) conjugate 500, in an embodiment of the present invention. The block diagram of the BRET-LN conjugate 500 depicts a semiconductor nanostructure 502, such as a bioluminescent resonance energy transfer acceptor molecule, linked to a luminescent enzyme 504, such as a bioluminescent enzyme or a chemiluminescent enzyme acting as a bioluminescent resonance energy transfer donor molecule. The luminescent enzyme 504 may be held in position by a spacing molecule 506. The luminescent enzyme 504 must be held with in a Foster distance 508, usually between 10 and 100 Angstrom, in order to allow the Bioluminescent Resonant Energy Transfer to take place.

In an example of the luminescent nanocrystal 500, the semiconductor nanostructure 502 may be linked, at the Foster distance 508 of 30 Angstroms, to the luminescent enzyme 504, such as a Renilla luciferase, that may emit at a wavelength of 480 nm. When the luminescent nanocrystal 500 is activated, the luminescent enzyme 504 will activate the semiconductor nanostructure 502 through the Bioluminescent Resonance Energy Transfer. The semiconductor nanostructure 502 may be formulated to provide the light emission 118, of FIG. 1, at a wavelength of 600 nm to 900 nm In the previous example, the use of Bioluminescent Resonance Energy Transfer (BRET) conjugates composed of the luminescent nanocrystal 500 such as the semiconductor nanostructure 502 closely linked to the luminescent enzyme 504 that employs the adenosine triphosphate (ATP) molecule (not shown) as a co-substrate, such as the Renilla luciferase. In the preferred implementation of the invention, the BRET-LN conjugate 500 would incorporate a mutant form of the luminescent enzyme 504 optimized for maximum stability.

In a preferred embodiment of the invention the semiconductor nanostructure 502 that may emit in the red visible light spectrum will be used as a BRET acceptor molecule. Emissions at wavelengths longer than 650 nm minimize the possibility of exciting auto-fluorescence of blood proteins such as hemoglobin.

There are many ways to achieve a stable linkage between the semiconductor nanostructure 502 and the luminescent enzyme 504. One method is to form a stable amide linkage between the two molecules using 1-ethyl-3-(3-dimethylaminopropyl) carbodiimide hydrochloride (EDC) as a coupling reagent. A second method that has the potential to better retain the activity of the luminescent enzyme 504 is to add a histadine tag to the luminescent enzyme 504, and conjugate nickel-nitrilotriacetate (NTA) to the semiconductor nanostructure 502 in the presence of nickel ions. A third method involves using a streptavidin-biotin bond, with streptavidin on the surface of the semiconductor nanostructure 502 and biotin-conjugated with the luminescent enzyme 504. There are many other methods that could be employed to create the BRET-LN conjugate incorporating Luciferin.

Figure 6:
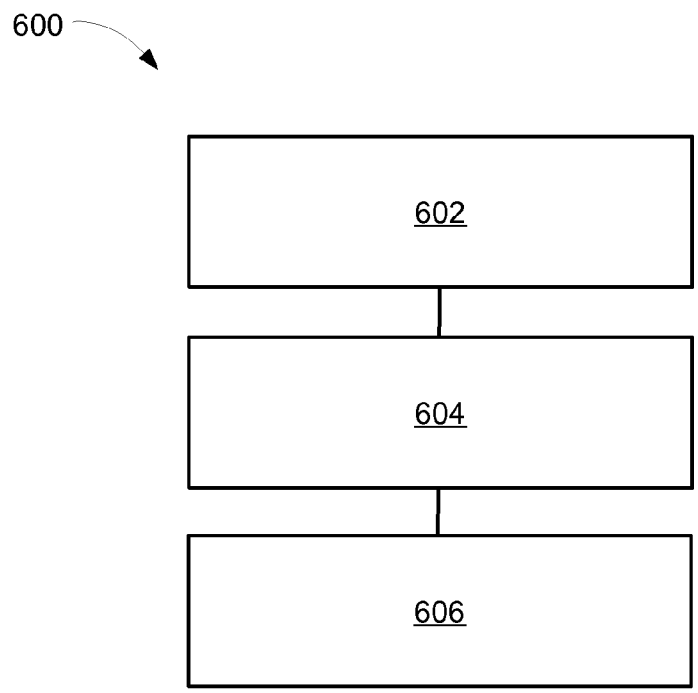
FIG. 6 is a flow chart of an enzyme detection system for operating the enzyme detection system with caged substrates, in an embodiment of the present invention.

Referring now to FIG. 6, therein is shown a flow chart of an enzyme detection system 600 for operating the enzyme detection system with caged substrates, in an embodiment of the present invention. The system 600 includes forming a caged substrate in a block 602; releasing an uncaged substrate by cleaving a caging molecule from the caged substrate in a block 604; and emitting a light emission from a Bioluminescence Resonance Energy Transfer luminescent nanocrystal conjugate reacting with the uncaged substrate in a block 606.

It has been discovered that the present invention thus has numerous aspects.

The invention is the specific modification of the coelenterazine molecule at either of two potential attachment points containing a hydroxyl molecule. The covalent addition of an enzyme-cleavable molecule, such as a phosphate group, to either of this attachment points inactivates coelenterazine as a substrate for the reaction catalyzed by Renilla luciferase. The enzyme-cleavable group is chosen for specificity to a given enzyme, for example, a phosphate group for specificity to alkaline phosphatase (ALP), which may be present in a whole blood sample. Cleavage of the added group due to the catalytic action of the enzyme of interest, such as the alkaline phosphatase (ALP), activates the coelenterazine as a substrate for the reaction catalyzed by Renilla luciferase, creating light emission, such as a bioluminescent light output, that can be correlated to the presence and activity of the cleaving enzyme. In this example the cleaving enzyme may be alkaline phosphatase (ALP).

A principle aspect that has been unexpectedly discovered is that the present invention is that the inventive hydrolase assays may be implemented as homogeneous or heterogeneous assays in open platform such as well-plate readers or high-throughput clinical chemistry analyzers, or in microfluidic format or microarray format. When implemented as a heterogeneous assay, the BRET-LN conjugate is immobilized on a surface directly or linked to the surface through n spacer arm. The surface material may be glass, noble metals, thin-film dielectrics, ceramics, plastics, and any other material that that can be functionalized to provide a chemical link between the surface and a luminescent nanocrystal. The surface-linked BRET-LN conjugates may be surrounded by pegylated surfaces or any other anti-fouling film that prevents non-specific binding Another important aspect of the present invention is that it valuably supports and services the historical trend of reducing costs, simplifying systems, and increasing performance.

These and other valuable aspects of the present invention consequently further the state of the technology to at least the next level.

Thus, it has been discovered that the enzyme detection system with caged substrates of the present invention furnishes important and heretofore unknown and unavailable solutions, capabilities, and functional aspects for detecting the measurement of Alkaline Phosphatase (ALP) activity in whole blood. The resulting processes and configurations are straightforward, cost-effective, uncomplicated, highly versatile and effective, can be surprisingly and unobviously implemented by adapting known technologies, and are thus readily suited for efficiently and economically manufacturing enzyme analysis devices fully compatible with conventional manufacturing processes and technologies.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the scope of the included claims. All matters hithertofore set forth herein or shown in the accompanying drawings are to be interpreted in an illustrative and non-limiting sense.

What is claimed is:

1. A qualitative and quantitative hydrolase detection method comprising:
   providing a caged coelenterazine molecule having a caging molecule bonded to at least one bonding site of the coelenterazine molecule;
   activating a coelenterazine molecule by cleaving the caging molecule from the caged coelenterazine molecule with a hydrolase enzyme;
   determining a light emission from a Bioluminescence Resonance Energy Transfer luminescent nanocrystal conjugate reacting with the coelenterazine molecule activated in the presence of the hydrolase enzyme; and
   correlating the light emission for quantitatively and qualitatively determining the presence of the hydrolase enzyme.

2. The method as claimed in claim 1 further comprising detecting a phosphatase molecule.

3. The method as claimed in claim 1 further comprising forming the Bioluminescence Resonance Energy Transfer luminescent nanocrystal conjugate including forming a bioluminescent resonance energy transfer acceptor molecule.

4. The method as claimed in claim 1 wherein providing the caged coelenterazine molecule having the caging molecule bonded to at least one bonding site of the coelenterazine molecule includes bonding a first bonding site of the coelenterazine molecule with the caging molecule or bonding a second bonding site of the coelenterazine molecule with the caging molecule.

5. The method as claimed in claim 1 wherein releasing determining a light emission from a Bioluminescence Resonance Energy Transfer luminescent nanocrystal conjugate includes energizing a luminescent enzyme in the Bioluminescence Resonance Energy Transfer luminescent nanocrystal conjugate.

6. A qualitative and auantitative hydrolase detection composition comprising:
   a caged coelenterazine molecule having a caging molecule bonded to at least one bonding site of a coelenterazine molecule;
   a hydrolase enzyme for activating the coelenterazine molecule by cleaving the caging molecule from the caged coelenterazine molecule with the hydrolase enzyme; and
   a Bioluminescence Resonance Energy Transfer luminescent nanocrystal conjugate for detecting the hydrolase enzyme based on correlating a light emission from the Bioluminescence Resonance Energy Transfer luminescent nanocrystal conjugate reacted with the coelenterazine molecule activated in the presence of the hydrolase enzyme for quantitatively and qualitatively determining the presence of the enzyme.

7. The composition as claimed in claim 6 wherein the hydrolase enzyme is a phosphatase molecule for activating the coelenterazine molecule.

8. The composition as claimed in claim 6 wherein the Bioluminescence Resonance Energy Transfer luminescent nanocrystal conjugate includes a bioluminescent resonance energy transfer acceptor molecule.

9. The composition as claimed in claim 6 wherein the caged coelenterazine molecule having the caging molecule bonded to at least one bonding site of the coelenterazine molecule includes the caging molecule bonded to a first bonding site or a second bonding site of the coelenterazine molecule.

10. The composition as claimed in claim 6 wherein the the Bioluminescence Resonance Energy Transfer luminescent nanocrystal conjugate includes a luminescent enzyme energized in the Bioluminescence Resonance Energy Transfer luminescent nanocrystal conjugate.

11. The composition as claimed in claim 6 wherein:
the light emission correlates to the amount of the hydrolase enzyme; and
the caging molecule is a phosphate group.

12. The composition as claimed in claim 11 wherein the hydrolase enzyme is an alkaline phosphatase (ALP) molecule.

13. The composition as claimed in claim 11 wherein the Bioluminescence Resonance Energy Transfer luminescent nanocrystal conjugate includes a bioluminescent resonance energy transfer acceptor molecule including a semiconductor nanostructure.

14. The composition as claimed in claim 11 wherein the caged coelenterazine molecule having at least one bonding site includes a hydroxyl group at a first bonding site or a second bonding site of the coelenterazine molecule replaced with the phosphate group.

15. The composition as claimed in claim 11 wherein the Bioluminescence Resonance Energy Transfer luminescent nanocrystal conjugate includes a luminescent enzyme energized in the Bioluminescence Resonance Energy Transfer luminescent nanocrystal conjugate and including a semiconductor nanostructure for emitting the light emission at a wavelength in the range of 600 nm to 900 nm.

16. A qualitative and quantitative hydrolase detection method comprising:
forming a caged coelenterazine molecule including:
providing a coelenterazine molecule having at least one bonding site, and
bonding a phosphate group to the at least one bonding site of the coelenterazine molecule for forming the caged coelenterazine molecule;
activating the coelenterazine molecule by cleaving the phosphate group from the caged coelenterazine molecule with a hydrolase enzyme which removes the phosphate group from the coelenterazine molecule; and
determining a light emission from a Bioluminescence Resonance Energy Transfer luminescent nanocrystal conjugate reacting with the coelenterazine molecule activated in the presence of the hydrolase enzyme; and correlating the light emission for quantitatively and qualitatively determining the presence of the hydrolase enzyme.

17. The method as claimed in claim 16 further comprising detecting an alkaline phosphatase (ALP) molecule.

18. The method as claimed in claim 16 further comprising forming the Bioluminescence Resonance Energy Transfer luminescent nanocrystal conjugate including forming a bioluminescent resonance energy transfer acceptor molecule including forming a semiconductor nanostructure.

19. The method as claimed in claim 16 wherein forming the caged coelenterazine molecule having at least one bonding site includes replacing a hydroxyl group of a first bonding site or a second bonding site of the coelenterazine molecule with the phosphate group.

20. The method as claimed in claim 16 wherein determining the light emission includes energizing a luminescent enzyme in the Bioluminescence Resonance Energy Transfer luminescent nanocrystal conjugate and stimulating a semiconductor nanostructure for emitting the light emission at a wavelength in the range of 600 nm to 900 nm.

* * * * *

UNITED STATES PATENT AND TRADEMARK OFFICE
CERTIFICATE OF CORRECTION

PATENT NO. : 8,530,178 B2
APPLICATION NO. : 12/445378
DATED : September 10, 2013
INVENTOR(S) : Sobek et al.

It is certified that error appears in the above-identified patent and that said Letters Patent is hereby corrected as shown below:

In the Claims:

Column 6, claim 5, line 45, delete "wherein releasing determining a light emission" and insert therefor --wherein determining a light emission--

Column 6, claim 6, line 51, delete "auantitative hydrolase" and insert therefor --quantitative hydrolase--

Column 6, claim 6, line 67, insert --hydrolase-- before "enzyme."

Signed and Sealed this
Thirteenth Day of May, 2014

Michelle K. Lee
*Deputy Director of the United States Patent and Trademark Office*